(12) United States Patent
Niitsuma et al.

(10) Patent No.: US 8,434,226 B2
(45) Date of Patent: *May 7, 2013

(54) METHOD FOR MANUFACTURING A HEAT EXCHANGER

(75) Inventors: Tomokazu Niitsuma, Hiroshima (JP); Minoru Tanaka, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 123 days.

This patent is subject to a terminal disclaimer.

(21) Appl. No.: 13/070,635

(22) Filed: Mar. 24, 2011

(65) Prior Publication Data

US 2011/0203111 A1    Aug. 25, 2011

Related U.S. Application Data

(62) Division of application No. 12/087,360, filed as application No. PCT/JP2006/325871 on Dec. 26, 2006.

(30) Foreign Application Priority Data

Jan. 6, 2006 (JP) .................................. 2006-001775

(51) Int. Cl.
*B21D 53/06* (2006.01)
(52) U.S. Cl.
USPC ............. 29/890.035; 29/890.03; 29/890.034; 165/157; 165/158
(58) Field of Classification Search .............. 29/890.03–890.054; 165/158, 157, 175
See application file for complete search history.

(56) References Cited

U.S. PATENT DOCUMENTS

| | | | |
|---|---|---|---|
| 4,416,841 A | 11/1983 | Corea et al. |
| 4,479,769 A | 10/1984 | Simioni |
| 4,560,523 A | 12/1985 | Plumley et al. |
| 4,689,191 A | 8/1987 | Beck et al. |
| 6,113,782 A | 9/2000 | Leonard |
| 6,180,038 B1 | 1/2001 | Cesaroni |
| 6,575,731 B1 | 6/2003 | Olaru et al. |

(Continued)

FOREIGN PATENT DOCUMENTS

| | | | |
|---|---|---|---|
| EP | 1715279 A1 | 10/2006 |
| EP | WP 1 715 279 A1 | 10/2006 |

(Continued)

*Primary Examiner* — Richard Chang
(74) *Attorney, Agent, or Firm* — Hamre, Schumann, Mueller & Larson, P.C.

(57) ABSTRACT

A heat exchange module 12 is formed by stacking pipe groups obtained by fixing a plurality of pipes 1 with use of pipe array holding members 9a to 9d. Flow path forming members 50 are arranged on pipe groups in the uppermost and lowermost layers, and walls 51 and 52 are provided so as to protrude from the outer-side pipe array holding members and the inner-side pipe array holding members. Flow path members 63 are provided between the walls 51 and 52 adjacent to each other so as to allow through holes 53 and 54 to communicate with each other. The heat exchange module 12 is housed in the housing 2, and while rotating the housing 2, a resin material 24 is filled into a space enclosed by the two inner-side pipe array holding members of each pipe group in the housing 2, interstices around the pipes present between an opening 15a of the housing and the outer-side pipe array holding members, and interstices around the pipes present between an opening 15b of the housing and the outer-side pipe array holding members.

8 Claims, 14 Drawing Sheets

U.S. PATENT DOCUMENTS

| | | |
|---|---|---|
| 6,872,346 B2 | 3/2005 | Stillig |
| 8,104,303 B2 * | 1/2012 | Murata et al. .................. 62/290 |
| 8,161,645 B2 * | 4/2012 | Palmieri .................. 29/890.033 |
| 2006/0228442 A1 | 10/2006 | Fischer et al. |

FOREIGN PATENT DOCUMENTS

| | | |
|---|---|---|
| JP | 55-134297 | 10/1980 |
| JP | 58-160658 | 5/1985 |
| JP | 60-71890 | 5/1985 |
| JP | 61-124638 | 8/1986 |
| JP | 61-285396 | 12/1986 |
| JP | 3-236856 | 10/1991 |
| JP | 2000-511830 | 9/2000 |
| JP | 2003-14397 | 1/2003 |
| JP | 2005-224301 | 8/2005 |
| WO | WO 2005/75922 A1 | 8/2005 |

* cited by examiner

METHOD FOR MANUFACTURING A HEAT EXCHANGER

This application is a division of application U.S. Ser. No. 12/087,360, filed Jul. 2, 2008, which is a U.S. National Stage application of International Application No. PCT/JP2006/325871, filed Dec. 26, 2006, which application is hereby incorporated herein by reference.

TECHNICAL FIELD

The present invention relates to a heat exchanger, particularly to a heat exchanger used in medical equipment such as a heart-lung machine, a heart-lung machine equipped with the same, a method for manufacturing the heat exchanger, and a method for manufacturing a heart-lung machine.

BACKGROUND ART

In heart surgery that involves cardiac arrest in a patient, a heart-lung machine is used for taking over the functions of respiration and circulation during the cardiac arrest. Further, during the surgery, it is necessary to lower the patient's temperature and maintain the same so that the patient's oxygen consumption should decrease. For this purpose, the heart-lung machine is equipped with a heat exchanger to control the temperature of blood taken out of the patient.

As such a medical-use heat exchanger, a bellows-type heat exchanger, a multi-tubular heat exchanger (see Patent Document 1, for instance), etc., have been known conventionally. Among these, the multi-tubular heat exchanger has a larger area used for heat exchange as compared with the bellows-type heat exchanger with the same device capacity, and hence, it has the advantage of a higher heat exchange ratio as compared with the bellows-type heat exchanger.

Here, an example of the conventional multi-tubular heat exchanger is described specifically with reference to FIGS. 9A to 9C, and 10. FIGS. 9A to 9C show a configuration of a conventional heat exchanger. FIGS. 9A, 9B, and 9C are a top view, a side view, and a front view of the same, respectively. FIG. 10 is a partially cut-off perspective view illustrating the inside of a housing of the heat exchanger shown in FIGS. 9A to 9C.

As shown in FIGS. 9A to 9C, the conventional heat exchanger includes a plurality of pipes 1 through which cold/hot water flows, a housing 102 for housing the pipes, and sealing members 103a to 103c for sealing blood flowing over surfaces of the plurality of pipes 1. Further, as shown in FIGS. 9A to 9C and 10, the plurality of pipes 1 are arranged in parallel with one another in the housing 102.

Still further, the housing 102 includes an inlet 104 for introducing blood into the housing, and a first outlet 105 for discharging blood out of the housing. The inlet 104 is an inlet of a flow path 108 of blood, while the first outlet 105 is an outlet of the flow path 108 of blood, which will be described later.

Further, as shown in FIG. 10, in the heat exchanger, there are a first sealing member 103a positioned on one of end sides of the plurality of pipes 1, a second sealing member 103b positioned on the other end side of the pipes, and a third sealing member 103c positioned between the first and second sealing members 103a and 103b. The first, second, and third sealing members 103a, 103b, and 103c are involved in the sealing among the pipes 1.

The third sealing member 103c is provided so that a gap 7 is provided between the third sealing member 103c and the first sealing member 103a, as well as a gap 7 is provided between the third sealing member 103c and the second sealing member 103b. Further, as shown in FIGS. 9A to 9C, the flow path 108 is formed in the third sealing member 103c so that blood introduced from the inlet 104 into the housing 2 is guided to the first outlet 105. The third sealing member 103c provides a sealing for blood. Further, the housing 102 is provided with second outlets 106 in a manner such that the second outlets 106 communicate with the gaps 7.

Therefore, in the conventional heat exchanger shown in FIGS. 9A to 9C, in the case where, for example, blood leaks due to seal leakage of the third sealing member 103c, the blood having leaked is retained temporarily in the gaps 7, and thereafter is discharged through the second outlets 106 to outside the heat exchanger. In the case where cold/hot water leaks due to seal leakage of the first sealing member 3a or the second sealing member 3b, the cold/hot water having leaked is retained temporarily in the gap 7, and thereafter is discharged through the second outlets 106 to outside the heat exchanger. As a result, according to the heat exchanger shown in FIGS. 9A to 9C, in both the cases where blood leaks and where cold/hot water leaks, the leakage through the sealing can be detected immediately, and further, the occurrence of blood contamination can be prevented.

It should be noted that in FIGS. 9A to 9C, 114 and 115 denote injection holes for filling a material for forming the sealing members, which are provided on the top face of the housing 102, and 116 and 117 denote air vents used upon the filling of the material for forming the sealing members, which are formed on side faces of the housing 102. The injection holes 114 and 115, and the air vents 116 and 117 are described later.

Next, as to a series of principal steps of a process for manufacturing the conventional heat exchanger shown in FIGS. 9A to 9C and 10 are described below, with reference to FIGS. 11 to 14. FIGS. 11A to 11C show pipe groups composing a heat exchange module; FIGS. 11A, 11B, and 11C are a top view, a front view, and a perspective view, respectively. FIGS. 12A, 12B, and 12C are a heat exchange module composed of a plurality of pipes; FIGS. 12A to 12C are a top view, a front view, and a perspective view, respectively. FIG. 13 is a top view illustrating the state in which the housing is attached to a jig so that sealing members are formed. FIG. 14 is a cross-sectional view showing a step for, forming the sealing members.

First, as shown in FIGS. 11A to 11C, a pipe group 10 is formed, which includes two or more (nine in the example shown in FIGS. 11A to 11C) pipes 1 arrayed in a row in parallel with one another, and pipe array holding members 9a to 9d, each of which is present in gaps between the pipes and holds the array of the pipes 1. In the pipe group 10, the pipe array holding members 9a to 9d are in a state of being pierced by the pipes 1, whereby the array of the pipes 1 is held. The pipe array holding members 9 are formed in a belt-like shape, and the two or more pipes 1 are arrayed in a row in the lengthwise direction of the belt. Further, four of the pipe array holding members 9 are arranged along the central axes of the pipes 1.

In the example shown in FIGS. 11A to 11C, the pipe group 10 is formed by pouring a resin into a die in which the two or more pipes 1 are arranged so that the pipe array holding members 9a to 9d are formed; that is, the pipe group 10 is formed by insert molding. A plurality of the pipe groups 10 are produced. Further, the pipe array holding members 9a to 9d are provided with a plurality of recessed portions 11.

Next, as shown in FIGS. 12A to 12C, a heat exchange module 12 is formed by stacking a plurality of pipe groups 10. Here, the pipes 1 composing each pipe group 10 are fitted in the recessed portions 11 provided at the pipe array holding members 9a to 9d of the pipe groups adjacent to each other in the vertical direction.

Further, in order to prevent the resin material flowing into the gaps 7 in the step of forming the sealing members by filling a resin material, which will be described later (see FIGS. 13 and 14), the pipe array holding member 9a of each pipe group 10 is brought into close contact with the pipe array holding members 9d of another pipe groups 10 immediately above and below the foregoing group. Likewise, the pipe array holding members 9b, 9c, and 9d of each pipe group 10 are brought into close contact with the pipe array holding members 9e, 9b, and 9a of another pipe groups 10 immediately above and below the foregoing group, respectively. The close contact is achieved by using an adhesive.

Next, the heat exchange module 12 shown in FIGS. 12A to 12C is housed in the housing 102. Here, the heat exchange module 12 is fixed in a state such that portions of the pipe array holding members 9a to 9d of each pipe group 10, which are exposed on surfaces of the heat exchange module 12, adhere to inner surfaces of the housing 102 with use of an adhesive.

Next, as shown in FIG. 13, first, the housing 102 in which the heat exchange module 12 is housed is attached to a jig 118. The jig 118 is composed of a main body plate 118a, and a pair of pressing plates 118b and 118c that sandwich the housing 102 at opening thereof on both the sides thereof. Packings 119 are provided between the pressing plates 118b and 118c and the housing 102.

Further, the jig 118 is configured rotatably around, as the center, an axis that passes through the center of the inlet 104 and the center of the first outlet 105. On the top face of the housing 102, a mask 120 is attached, so that a resin material is prevented from intruding through the inlet 104. The mask 120 is provided with apertures so that the injection holes 114 and 115 are not closed.

Next, as shown in FIG. 14, an injection pot 121 is attached on the top face of the housing 102. The injection pot 121 includes flow paths 124 for guiding a resin material 123 injected into the injection pot 121 to the injection holes 114 and 115. Here, 122 denotes a lid of the injection pot. It should be noted that in FIG. 14, the heat exchange module 12 is shown as viewed from a side thereof.

Further, as shown in FIG. 14, the injection hole 115 shown in the left-side part of the drawing is, formed so as to communicate with interstices around the pipes 1 between the opening of the housing on the left side as viewed in the drawing and the outer-side pipe array holding member (9a or 9d) of each pipe group 10 on the left side as viewed in the drawing (hereinafter referred to as "first housing space"). On the other hand, the injection hole 115 shown in the right-side part of the drawing is formed so as to communicate with interstices around the pipes 1 between the opening of the housing on the right side as viewed in the drawing and the outer-side pipe array holding member (9d or 9a) of each pipe group 10 on the right side as viewed in the drawing (hereinafter referred to as "second housing space").

Further, the injection holes 114 are formed so as to communicate with interstices around the pipes 1 between the two inner-side pipe array holding members 9b and 9c of each pipe group 10 in the housing 2 (hereinafter referred to as "third housing space"). Thus, the resin material 123 in the injection pot 121 is filled exclusively in the first housing space, the second housing space, and the third housing space, whereby the gaps 7 (FIGS. 9A to 9C and 10) are formed. Further, the filling of the resin material is carried out while the jig 118 is being rotated, as described above. Therefore, with the centrifugal force caused by this rotation, the flow path 108 is formed in a cylindrical form as shown in FIG. 10.

Further, if the first and second housing spaces do not have an escape through which air goes out, when the filling of the resin material through the injection holes 115 is started, these spaces become completely closed spaces, and hence, the filling of the resin material becomes difficult. Therefore, as shown in FIGS. 9A to 9C, air vents 116 are provided on the side faces of the housing 102 so that the air vents communicate with the first and second housing spaces, respectively. In the example shown in FIG. 13, the air vents 116 are connected via pipes 125 with air vents 117 that are formed so as to communicate with the third housing space. Air squeezed out of the first and second housing spaces enters the third housing space, and then, is discharged through the inlet 104 or the outlet 105.

It should be noted that the function of the pipes 125 is not limited to this. Each capacity of the first and second housing spaces is smaller than the capacity of the third housing space, and the filling of the resin material into the first and second housing spaces ends earlier. Therefore, the pipes 125 also function for supplying excess resin material to the third housing space. In other words, in addition to the function of allowing the filling of the resin material to the first and second housing spaces to be performed smoothly, the pipes 125 also has the function of suppressing the waste of resin material, and the function of filling the third housing space with the resin material.

Thus, by injecting the resin material with use of the injection pot 121 shown in FIG. 14, the first sealing member 103a is formed in the first housing space, while the second sealing member 103b is formed in the second housing space. Further, in the third housing space, the third sealing member 103c is formed. Still further, since the resin material filled in the third housing space is subjected to the centrifugal force caused by the rotation of the jig 118, the flow path 108 is formed in the third housing space.

Patent document 1: JP 2005-224301 A

DISCLOSURE OF INVENTION

Problem to be Solved by the Invention

However, the above-described method for manufacturing the heat exchanger has a risk that the pipes 125 (see. FIG. 13) could be disengaged due to the rotation of the jig 118 for the filling of a resin material. In this case, the filling of the resin material has to be stopped temporarily, and the already filled resin material could possibly be cured before the filling operation is restarted. This makes it impossible to complete the product.

Still further, in the above-described method for manufacturing the heat exchanger, the resin material filled in the first and second housing spaces also is subjected to the centrifugal force caused by the rotation of the jig 118. As a result, a space in which a resin material is not filled (air reservoir) could occur in regions of the outer-side pipe array holding members 9a and 9b, on the sides of the ends of the pipe group 10 (see regions A and B shown in FIG. 12A). In this case, areas of adhesion of the pipe array holding members 9a, 9b with the resin material decrease, whereby the air tightness and durability of the sealing members 103a and 103b (see FIGS. 9A to 9C) decrease. Still further, it is very difficult, in a post-processing step, to fill a resin material into a space where a resin material has not been filled.

It is an object of the present invention to provide a heat exchanger in which the above-described problem is solved and the occurrence of an air reservoir at sealing portions is suppressed, a method for manufacturing this heat exchanger, and a method for manufacturing a heart-lung machine.

Means for Solving Problem

In order to achieve the above-described object, a method of the present invention for manufacturing a heat exchanger is a method for manufacturing a heat exchanger that includes pipes through which a first fluid flows, and a housing, wherein the housing has a pair of openings that expose ends of the pipes on both sides, an inlet for introducing a second fluid into the housing, and an outlet provided so as to be opposed to the inlet, the outlet being for discharging the second fluid, and the second fluid comes into contact with surfaces of the pipes. The method includes the steps of (a) forming a heat exchange module that includes a plurality of pipes arrayed in parallel with one another in a two-dimensional form, and fixing members that are present in interstices around the pipes to hold the array of the plurality of pipes, wherein four pieces of the fixing members are arranged along a central axis direction of the pipes with spaces therebetween; (b) providing walls on respective outer peripheral portions of the fixing members, wherein each of the walls has a through hole going through in a thickness direction of the wall, and protrudes toward outside of the heat exchange module; (c) arranging flow path members, each of which is arranged between the walls on the outer-side fixing member positioned closely to an end of the tube and on the inner-side fixing member adjacent to the outer-side fixing member so as to communicate with the through holes provided in the walls; (d) housing the heat exchange module into the housing, and bringing parts of the outer peripheral portions of the fixing members where the walls are not provided, and the walls, into close contact with inner surfaces of the housing; and (e) while rotating the housing around an axis that passes through the centers of the inlet and the outlet, filling a resin material into interstices around the pipes present between one of the openings of the housing and the outer-side fixing member adjacent thereto, interstices around the pipes present between the other opening of the housing and the outer-side fixing member adjacent thereto, and interstices around the pipes present between the two inner-side fixing members, and further, forming a flow path between the two inner-side fixing members through which the second fluid introduced through the inlet is guided to the outlet.

Further, in order to achieve the above-described object, a method of the present invention for manufacturing a heart-lung machine includes the above-described method of the present invention for manufacturing a heat exchanger.

Still further, in order to achieve the above-described object, a heat exchanger of the present invention includes a heat exchange module, a housing that houses the heat exchange module, and sealing members, wherein the heat exchange module includes a plurality of pipes through which a first fluid flows, and fixing members, wherein the plurality of pipes are arrayed in parallel with one another in a two-dimensional form, the fixing members are present in interstices around the pipes to hold the array of the plurality of pipes, and four pieces of the fixing members are arranged along a central axis direction of the pipes with spaces therebetween, and walls are provided on outer peripheral portions of the fixing members, each of the walls having a through hole going through in a thickness direction of the wall, and protruding toward outside of the heat exchange module; the housing has a pair of openings that expose ends of the pipes on both sides, an inlet for introducing a second fluid flowing over surfaces of the plurality of pipes into the housing, and an outlet disposed so as to be opposed to the inlet, the outlet being for discharging the second fluid, wherein inner surfaces of the housing are brought into close contact with parts of the outer peripheral portions of the fixing members where the walls are not provided, and with the walls; the sealing members include a first sealing member, a second sealing member, and a third sealing member, wherein the first sealing member is formed with a resin material filled in interstices around the pipes positioned between one of the openings of the housing on one side and the outer-side fixing member positioned closely to ends of the pipes on said side; the second sealing member is formed with a resin material filled in interstices around the pipes positioned between the other one of the openings of the housing on the other side and the outer-side fixing member positioned closely to ends of the pipes on the other side; the third sealing member is formed with a resin material filled in interstices around the pipes present between the two inner-side fixing members; and a flow path through which the second fluid introduced through the inlet is guided to the outlet is formed with the third sealing member between the two inner-side fixing members.

Effects of the Invention

As described above, in the present invention, when a resin material is filled, the first and second housing spaces are allowed to communicate with the third housing space via through holes of two adjacent walls, and flow path members arranged therebetween. The communication of the first and second housing spaces with the third housing space is performed so that a region where air reservoir tends to occur becomes a flow path for a resin material. Therefore, with the present invention, the occurrence of air reservoir can be suppressed, while the degradation of air tightness and durability of sealing members can be suppressed.

BRIEF DESCRIPTION OF DRAWINGS

FIGS. 1A, 1B, and 1C are a top view, a front view, and a perspective view, respectively.

FIG. 2A is a side view, FIG. 2B is a top view, FIG. 2C is a cross-sectional view taken along a cutting line A-A' in FIG. 2B, and FIG. 2D is a cross-sectional view taken along a cutting line B-B' in FIG. 2B.

FIG. 3A is a front view, and FIG. 3B is a cross-sectional view.

FIGS. 9A, 9B, and 9C are a top view, a side view, and a front view of the same, respectively.

FIGS. 11A, 11B, and 11C are a top view, a front view, and a perspective view, respectively.

FIGS. 12A to 12C are a top view, a front view, and a perspective view, respectively.

DESCRIPTION OF THE INVENTION

Figure 1A:
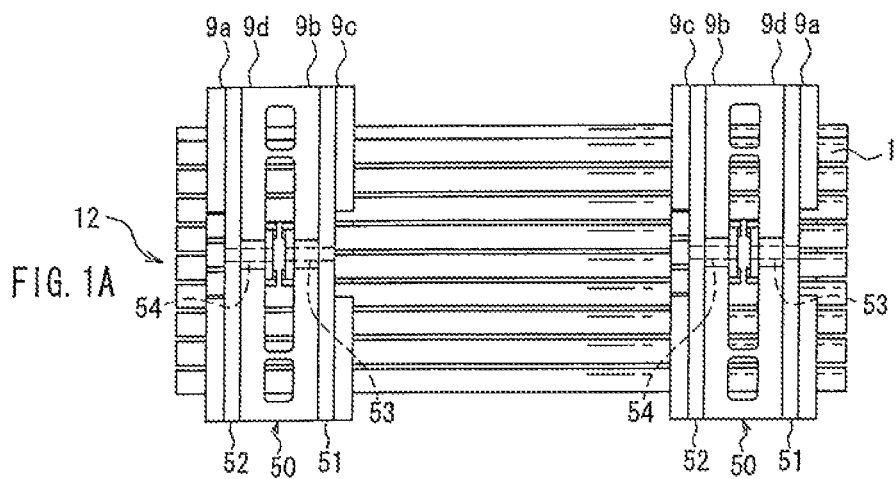
FIGS. 1A to 1C show a state in which flow path forming members are attached to a heat exchange module.

A method of the present invention for manufacturing a heat exchanger is a method for manufacturing a heat exchanger that includes pipes through which a first fluid flows, and a housing, wherein the housing has a pair of openings that expose ends of the pipes on both sides, an inlet for introducing a second fluid into the housing, and an outlet provided so as to be opposed to the inlet, the outlet being for discharging the second fluid, and the second fluid comes into contact with surfaces of the pipes. The method includes the steps of (a) forming a heat exchange module that includes a plurality of pipes arrayed in parallel with one another in a two-dimensional form, and fixing members that are present in interstices around the pipes to hold the array of the plurality of pipes, wherein four pieces of the fixing members are arranged along a central axis direction of the pipes with spaces therebetween; (b) providing walls on respective outer peripheral portions of the fixing members, wherein each of the walls has a through hole going through in a thickness direction of the wall, and protrudes toward outside of the heat exchange module; (c) arranging flow path members, each of which is arranged between the walls on the outer-side fixing member positioned closely to an end of the tube and on the inner-side fixing member adjacent to the outer-side fixing member so as to communicate with the through holes provided in the walls; (d) housing the heat exchange module in the housing, and bringing parts of the outer peripheral portions of the fixing members where the walls are not provided, and the walls, into close contact with inner surfaces of the housing; and (e) while rotating the housing around an axis that passes through the centers of the inlet and the outlet, filling a resin material into interstices around the pipes present between one of the openings of the housing and the outer-side fixing member adjacent thereto, interstices around the pipes present between the other opening of the housing and the outer-side fixing member adjacent thereto, and interstices around the pipes present between the two inner-side fixing members, and further, forming a flow path between the two inner-side fixing members through which the second fluid introduced through the inlet is guided to the outlet.

In the foregoing method of the present invention for manufacturing a heat exchanger, the following is preferable: in the step (a), the heat exchange module is formed by the steps of: forming a pipe group that includes two or more of the pipes arrayed in a row in parallel with one another, and pipe array holding members, each of which, is present in gaps between the pipes to hold the array of the two or more pipes, four pieces of the pipe array holding members being arranged along the central axis direction of the pipes with spaces therebetween; and stacking a plurality of the pipe groups, wherein the pipe array holding members of each pipe group are brought into close contact with the pipe array holding members of another pipe groups immediately above and below the said group in the central axis direction, so that the fixing members are formed with the pipe array holding members of the pipe groups, and in the step (b), on at least one of the pipe group positioned in an uppermost layer and the pipe group positioned in a lowermost layer, the walls are provided on the outer-side pipe array holding member positioned closely to the ends of the tubes and the inner-side pipe array holding member adjacent to the outer-side tube array holding member in a manner such that the walls are opposed to each other. This allows the formation of a heat exchange module to be carried out readily.

In the foregoing, the following is preferable: in the step (b), on both of the pipe group positioned in the uppermost layer and the pipe group positioned in the lowermost layer, the walls are provided on the two outer-side pipe array holding members and the two inner-side pipe array holding members. In this case, the occurrence of air reservoir can be suppressed further.

In the foregoing method of the present invention for manufacturing a heat exchanger, the following is preferable: the axis that passes through the centers of the inlet and the outlet perpendicularly crosses an axis that passes through the centers of the pair of openings, and the through holes are provided so as to be positioned on a line that is parallel with the axis that passes through the centers of the pair of openings, and that perpendicularly crosses a rotation axis of the housing. This is because in the foregoing case, a place on the line that is parallel with the axis that passes through the centers of the pair of openings and that perpendicularly crosses the rotation axis of the housing is the place where air reservoir is most likely to occur.

Further, it is also preferable that the foregoing method of the present invention for manufacturing a heat exchanger is further modified so as to include the step of removing the flow path members after the step (e). This makes it possible to seclude the third housing space from the first and second housing spaces, thereby isolating these spaces from one another. Therefore, it is possible to prevent the first fluid from going along the through holes of the walls and the flow path members and intruding into the third housing space, and to prevent the second fluid from going along the same and intruding into the first or second housing space.

Still further, in the above-described method of the present invention for manufacturing a heat exchanger, the following is preferable: the flow path members are formed with annular members having elasticity, and in the step (c), the annular members are fitted between the walls in a state of being deformed elastically. In this case, the flow path members can be brought into close contact with the walls, whereby fluid-tightness is ensured in the flow paths formed by the through holes of the two walls and the flow path members.

Still further, in the above-described method of the present invention for manufacturing a heat exchanger, the following is preferable: in the step (b), flow path forming members, each of which has two of the walls and is formed by connecting the walls in a state in which one wall and the other wall are opposed to each other, are arranged in a manner such that the one wall protrudes from the outer-side fixing member, while the other wall protrudes from the inner-side fixing member adjacent to the said outer-side fixing member. This makes the manufacture of a heat exchanger easier.

Still further, in the above-described method of the present invention for manufacturing a heat exchanger, the following is preferable: in the step (e), the resin material is supplied to the interstices around the pipes present between one of the openings of the housing and the outer-side fixing member adjacent thereto, and the interstices around the pipes present between the other opening of the housing and the outer-side fixing member adjacent thereto; and the resin material is supplied further to the interstices around the pipes present between the two inner-side fixing members via the through holes of the walls provided on the outer-side fixing members, the flow path members, and the through holes of the walls provided on the inner-side fixing members adjacent to the outer-side fixing members. This makes it possible further to suppress the occurrence of air reservoir.

Still further, a method of the present invention for manufacturing a heart-lung machine includes the above-described method of the present invention for manufacturing a heat exchanger.

A heat exchanger of the present invention includes a heat exchange module, a housing that houses the heat exchange module, and sealing members, wherein the heat exchange module includes a plurality of pipes through which a first fluid flows, and fixing members, wherein the plurality of pipes are arrayed in parallel with one another in a two-dimensional form, the fixing members are present in interstices around the pipes to hold the array of the plurality of pipes, and four pieces of the fixing members are arranged along a central axis direction of the pipes with spaces therebetween, and walls are provided on outer peripheral portions of the fixing members, each of the walls having a through hole going through in a thickness direction of the wall, and protruding toward outside of the heat exchange module, the housing has a pair of openings that expose ends of the pipes on both sides, an inlet for introducing a second fluid flowing over surfaces of the plurality of pipes into the housing, and an outlet disposed so as to be opposed to the inlet, the outlet being for discharging the second fluid, wherein inner surfaces of the housing are brought into close contact with parts of the outer peripheral portions of the fixing members where the walls are not provided, and with the walls, the sealing members include a first sealing member, a second sealing member, and a third sealing member, wherein the first sealing member is formed with a resin material filled in interstices around the pipes positioned between one of the openings of the housing on, one side and the outer-side fixing member positioned closely to ends of the pipes on said side, the second sealing member is formed with a resin material filled in interstices around the pipes positioned between the other one of the openings of the housing on the other side and the outer-side fixing member positioned closely to ends of the pipes on the other side, the third sealing member is formed with a resin material filled in interstices around the pipes present between the two inner-side fixing members, and a flow path through which the second fluid introduced through the inlet is guided to the outlet is formed with the third sealing member between the two inner-side fixing members.

The heat exchanger of the present invention preferably is configured so that the walls provided on the outer-side fixing members and the walls provided on the inner-side fixing members adjacent to the respective outer-side fixing members are formed so that flow path members can be disposed between the walls so as to communicate with the through holes of the walls. In the case where the heat exchanger of the present invention is configured as described above, the heat exchanger can be manufactured readily by the above-described method of the present invention for manufacturing a heat exchanger. Further, in this case, it is preferable that protrusions for positioning the flow path members are formed on a periphery of an opening, on the flow path member side, of the through hole of the wall provided on the outer-side fixing member, and on a periphery of an opening, on the flow path member side, of the through hole of the wall provided on the inner-side fixing member.

It also is preferable that the above-described heat exchanger of the present invention is configured so that the flow path members are formed with annular members having elasticity, and the walls provided on the outer-side fixing members and the walls provided on the inner-side fixing members adjacent to the respective outer-side fixing members are formed so that the annular members can be fitted between the walls in a state of elastic deformation. In the case where the above-described heat exchanger of the present invention is manufactured by the above-described method of the present invention for manufacturing a heat exchanger, the foregoing configuration makes it possible to bring the flow path members into close contact with the walls, whereby fluid-tightness is ensured in the flow paths formed by the through holes of the two walls and the flow path members.

Still further, the above-described heat exchanger of the present invention may be configured as follows: the heat exchange module is formed by stacking a plurality of pipe groups, each of the plurality of pipe groups includes two or more of the pipes arrayed in a row in parallel with one another, and pipe array holding members, each of which is present in gaps between the pipes to hold the array of the two or more pipes. Four pieces of the pipe array holding members are arranged along the central axis direction of the pipes with spaces therebetween. The pipe array holding members of each pipe group are brought into close contact with the pipe array holding members of another pipe groups immediately above and below the said group in the central axis direction, so as to form the fixing members, and on at least one of the pipe group positioned in an uppermost layer and the pipe group positioned in a lowermost layer, the walls are provided on the outer-side pipe array holding member positioned closely to ends of the pipes and the inner-side pipe array holding member adjacent to the outer-side pipe array holding member in a manner such that the walls are opposed to each other.

In the foregoing configuration, it is preferable that on both of the pipe group positioned in an uppermost layer and the pipe group positioned in a lowermost layer, the walls are provided on the two outer-side pipe: array holding members and the two inner-side pipe array holding members. In the case where the above-described heat exchanger of the present invention is manufactured by the above-described method of the present invention for manufacturing a heat exchanger, the occurrence of air reservoir can be suppressed further.

Embodiments

The following describes a heat exchanger and a method for manufacturing the same according to an embodiment of the present invention while referring to FIGS. 1 to 7. In the present embodiment, the heat exchanger is for use in medical equipment such as a heart-lung machine used for controlling the temperature of blood taken out of a patient.

Figure 1B:
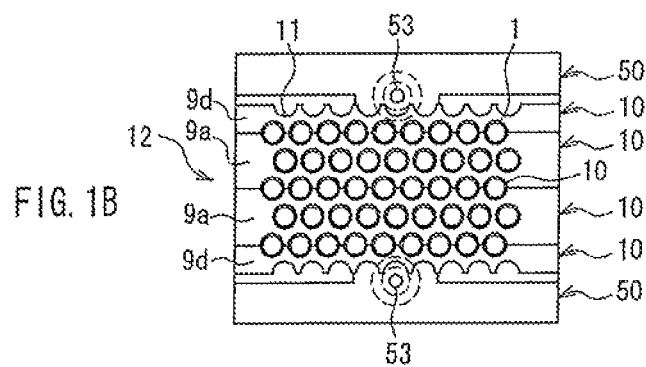
Figure 1C:
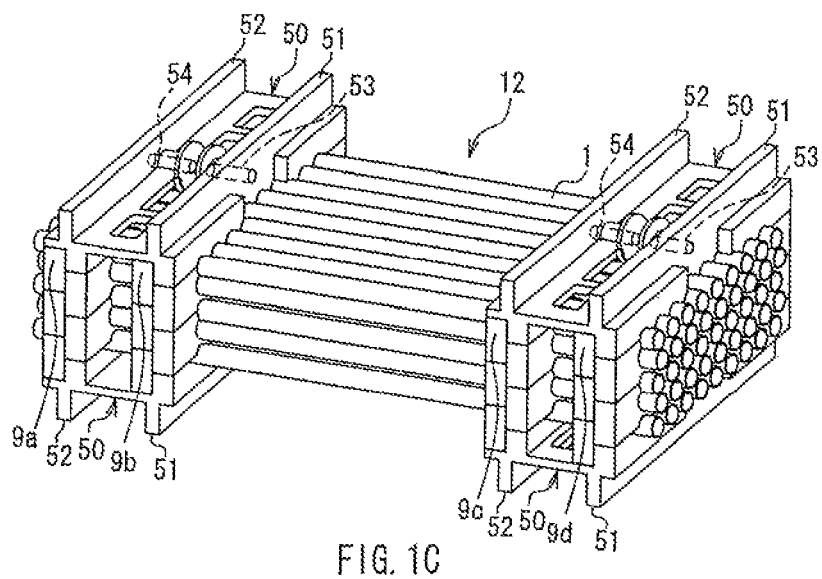
Figure 2A:
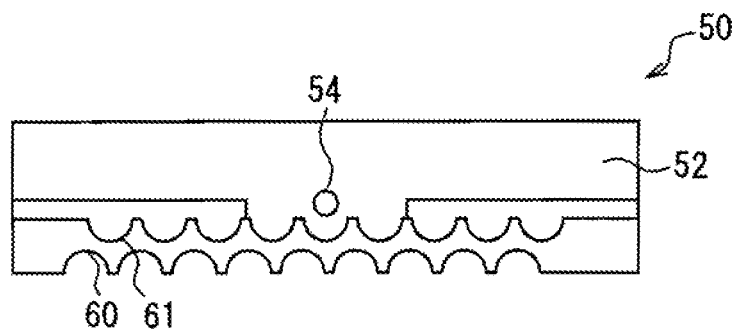
FIGS. 2A to 2D show a specific configuration of the flow path forming member shown in FIGS. 1A to 1C.
Figure 2B:
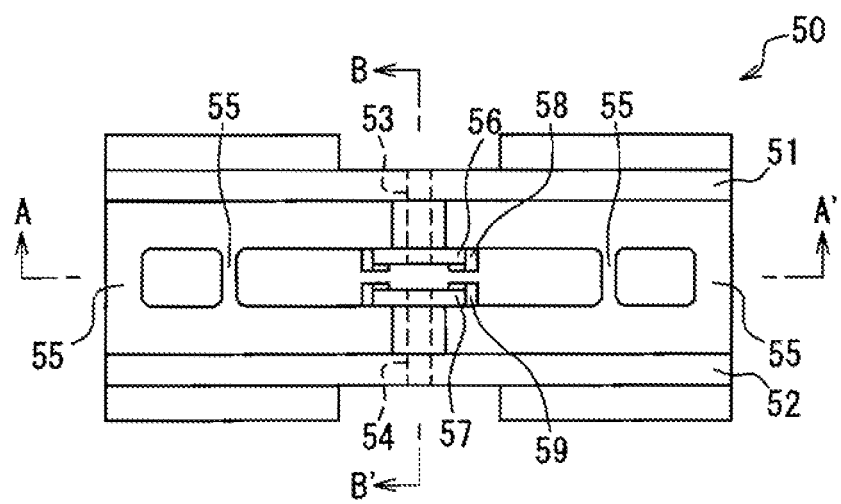
Figure 2C:
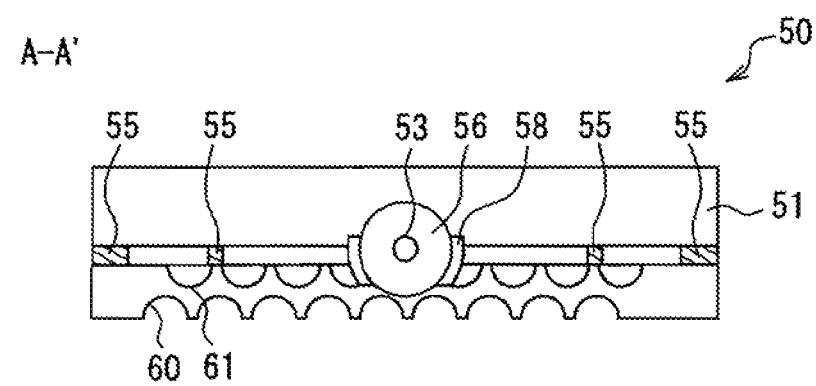
Figure 2D:
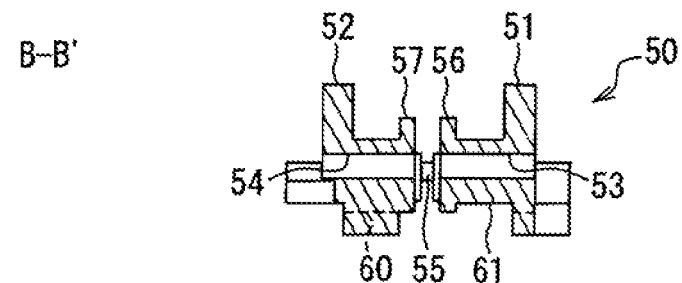
Figure 3A:
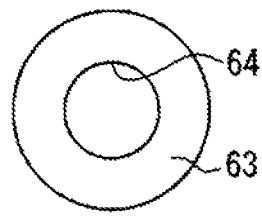
FIGS. 3A and 3B show a specific configuration of a flow path member.
Figure 3B:
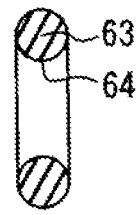

FIGS. 1A to 1C show a state in which flow path forming members are attached to a heat exchange module. FIGS. 1A, 1B, and 1C are a top view, a front view, and a perspective view, respectively. FIGS. 2A to 2D show a specific configuration of the flow path forming member shown in FIGS. 1A to 1C. FIG. 2A is a side view, FIG. 2B is a top view, FIG. 2C is a cross-sectional view taken along a cutting line A-A' in FIG. 2B, and FIG. 2D is a cross-sectional view taken along a cutting line B-B' in FIG. 2B. FIGS. 3A and 3B show a specific configuration of a flow path member. FIG. 3A is a front view, and FIG. 3B is a cross-sectional view.

Figure 4:
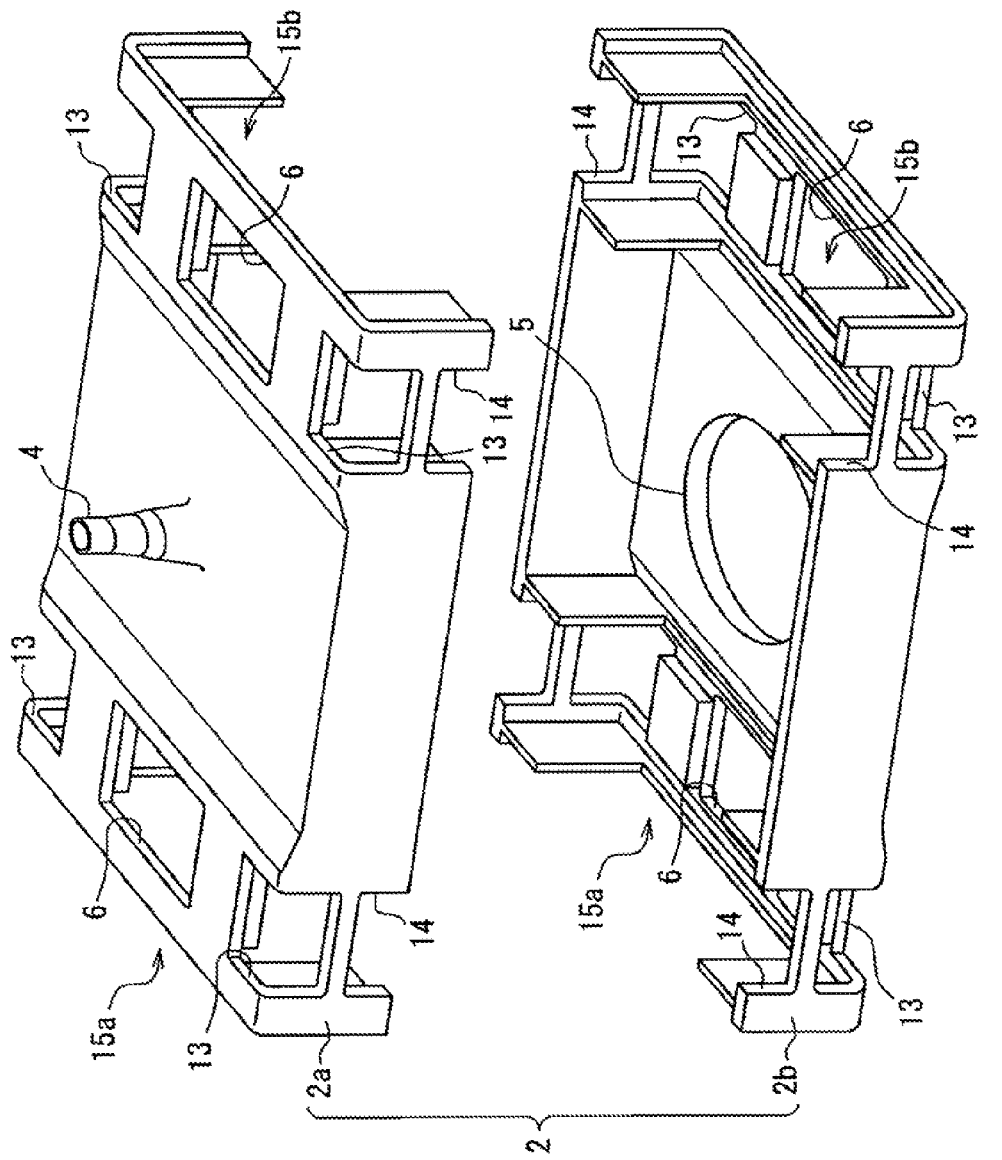
FIG. 4 is an exploded perspective view of a housing in which a heat exchange module is housed.
Figure 5:
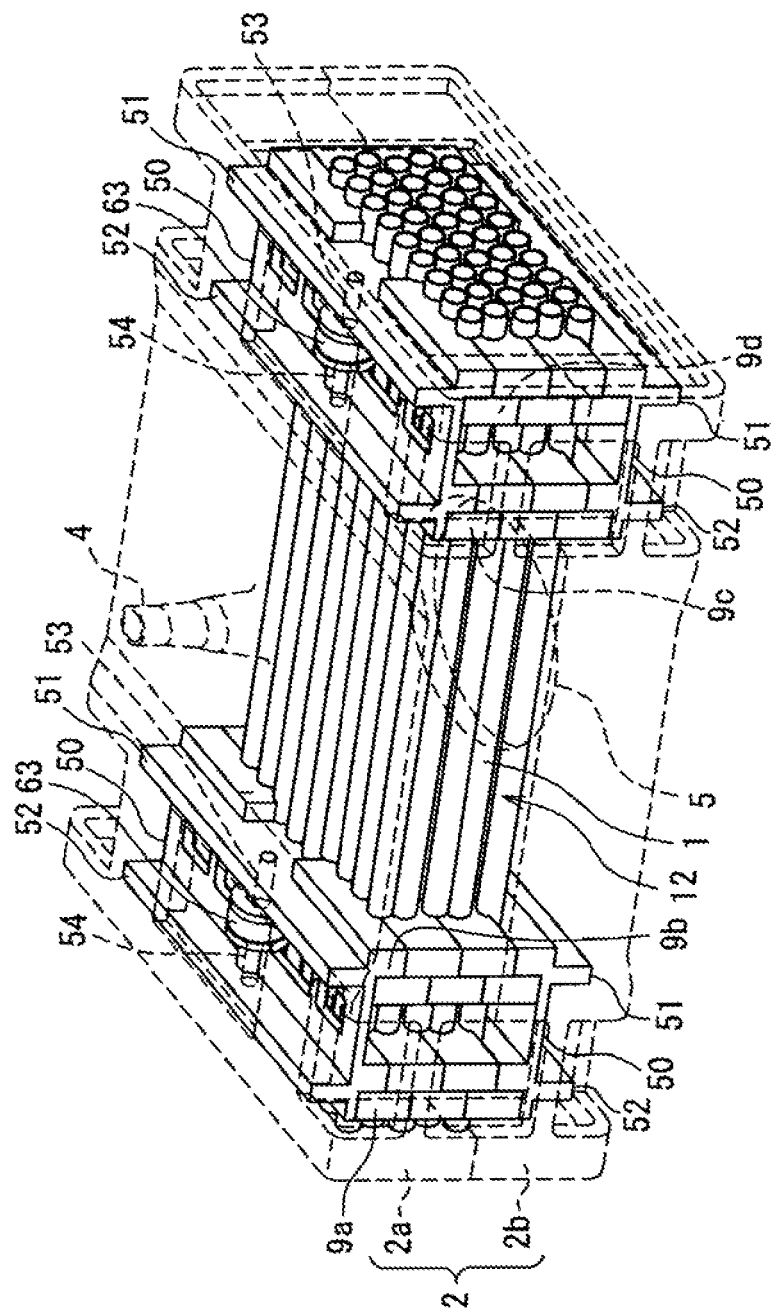
FIG. 5 is a perspective view showing a state in which the heat exchange module shown in FIGS. 1A to 1C is placed in the housing shown in FIG. 4.
Figure 6:
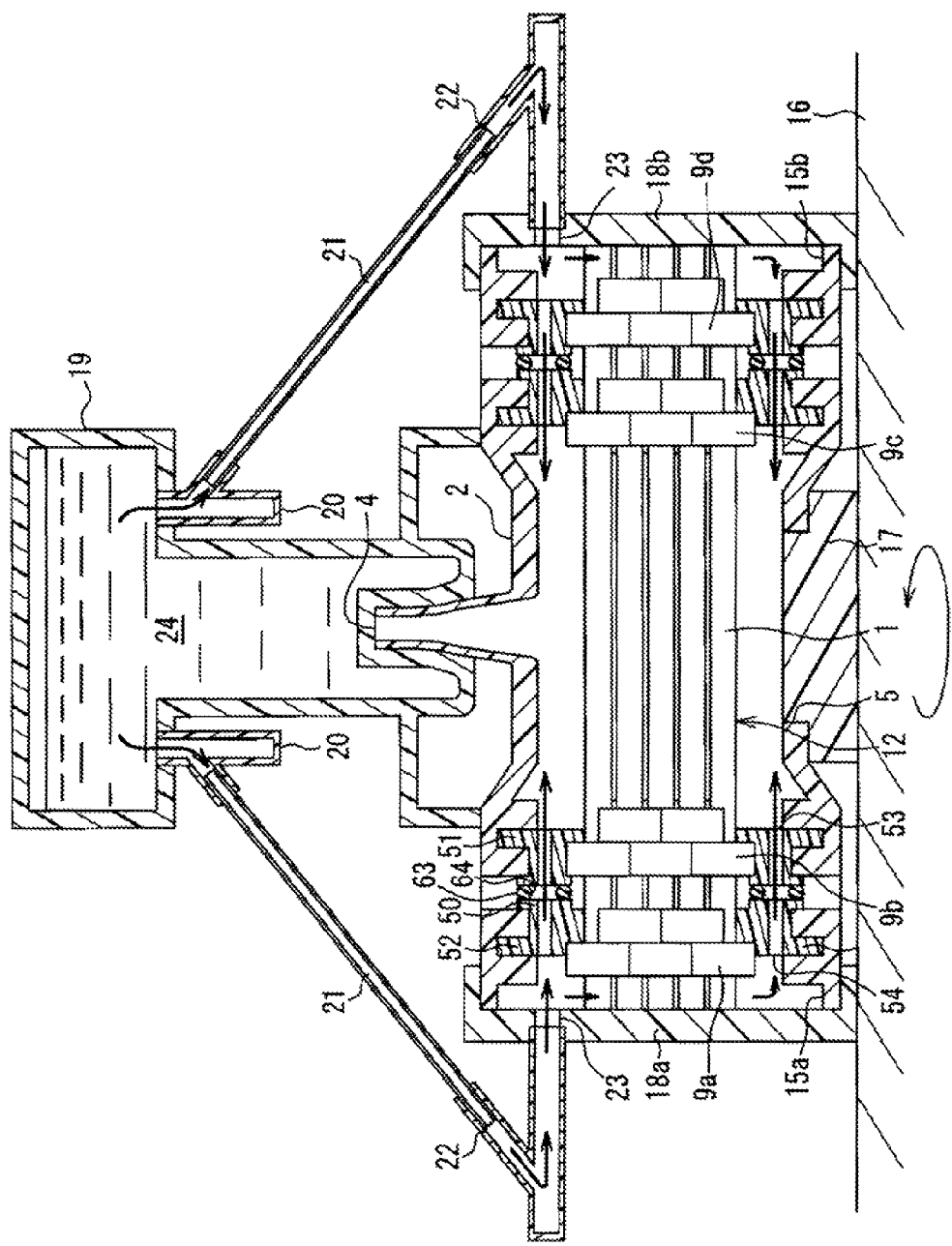
FIG. 6 is a cross-sectional view showing a step for forming a sealing member.
Figure 7:
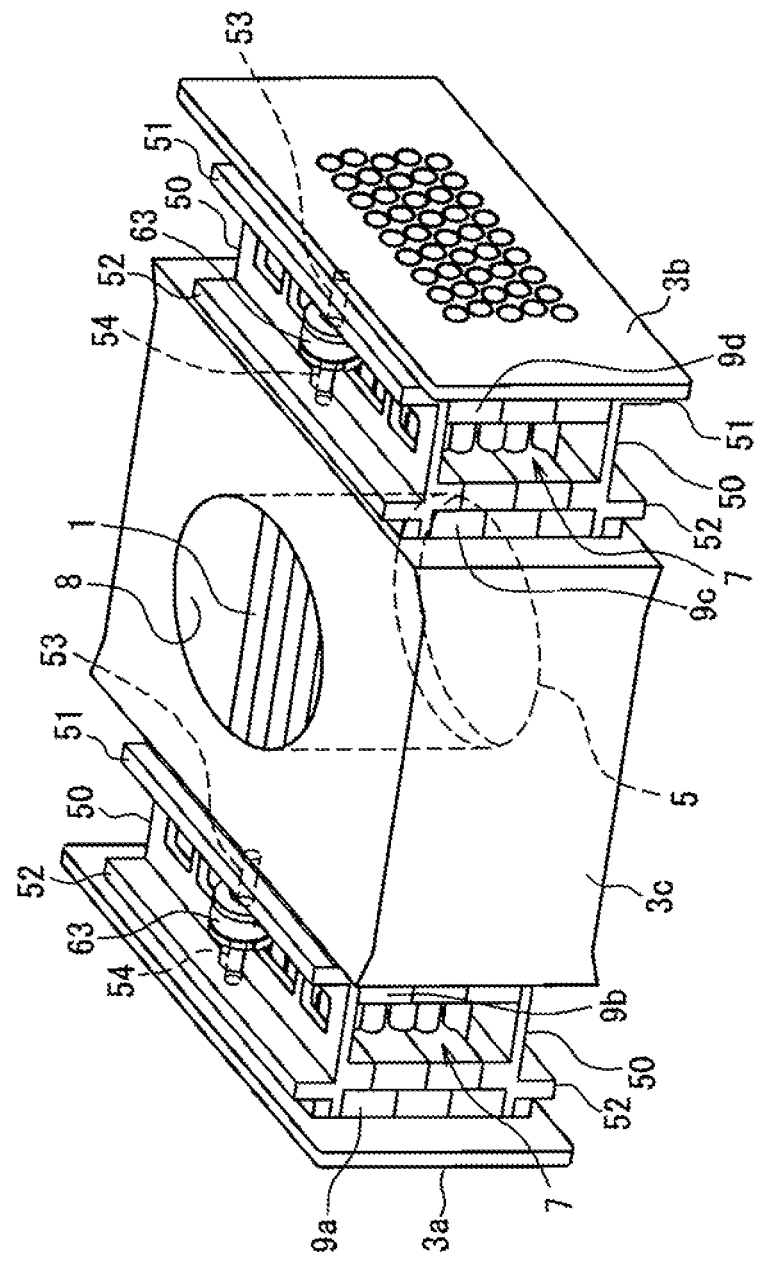
FIG. 7 is a perspective view showing a heat exchanger according to an embodiment of the present invention.

FIG. 4 is an exploded perspective view of a housing in which a heat exchange module is housed. FIG. 5 is a perspective view showing a state in which the heat exchange module shown in FIGS. 1A to 1C is placed in the housing shown in FIG. 4. FIG. 6 is a cross-sectional view showing a step for forming a sealing member. FIG. 7 is a perspective view showing a heat exchanger according to an embodiment of the present invention.

First, a method for manufacturing a heat exchanger according to the present embodiment is described with reference to FIGS. 1 to 6, and thereafter, the heat exchanger according to the present embodiment is described with reference to FIG. 7. It should be noted that in FIGS. 1A to 1C, and 4 to 7, portions denoted with the same reference numerals shown in FIGS. 9 to 14 described in the "Background Art" section are the same as the portions denoted with the foregoing reference numerals in FIGS. 9 to 14.

First, a heat exchange module 12 is formed, which includes a plurality of pipes 1 arrayed in parallel with one another in a two-dimensional form, and fixing members, each of which is present in interstices around the pipes to hold the plurality of pipes 1. In the present embodiment 1, the formation of the heat exchange module 12 is similar to that of the example shown in FIGS. 11 and 12 described in the "Background Art" section; first, a plurality of pipe groups 10 (see FIGS. 11A to 11C) are formed, each of which includes two or more pipes 1 and four pipe array holding members 9a to 9d; and subsequently, a heat exchange module 12 is formed by stacking these pipe groups 10 (see FIGS. 12A to 12C). In the present embodiment, cold/hot water for heat exchange flows through the insides of the pipes 1.

Figure 12A:
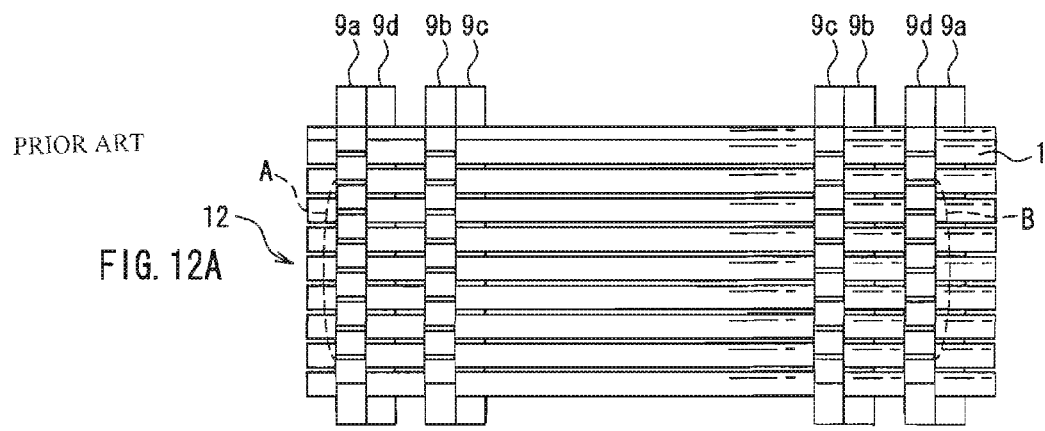
FIGS. 12A, 12B, and 12C are a heat exchange module composed of a plurality of pipes.
Figure 12B:
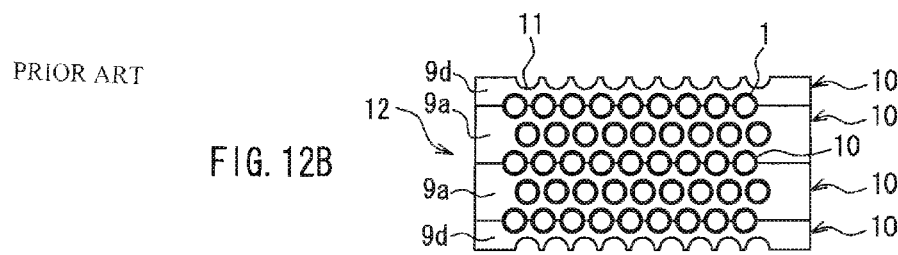
Figure 12C:
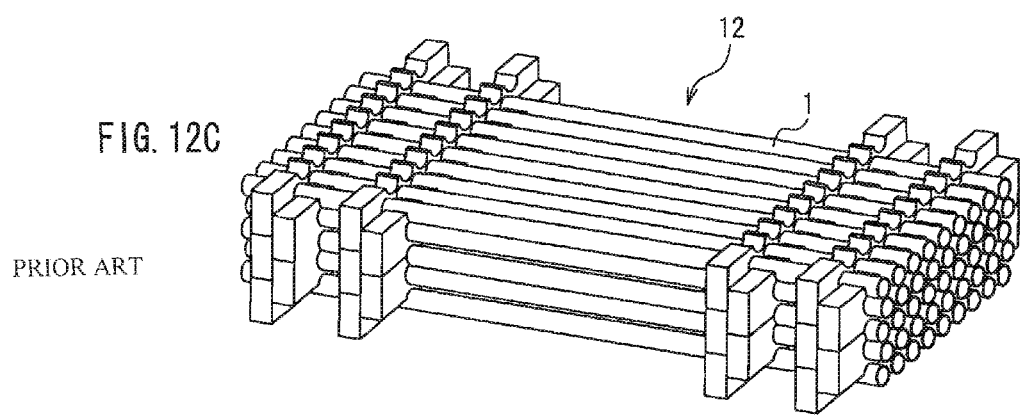

Further, in the present embodiment, a plurality of pipe array holding members 9a to 9d juxtaposed in the vertical direction, in close contact with each other, compose the above-described fixing members (see FIGS. 12A to 12C). The fixing members are pierced by the plurality of pipes 1 arrayed in parallel with one another in a two-dimensional form, thereby holding the two-dimensional array of the plurality of pipes 1.

It should be noted that in the present embodiment, the formation of the heat exchange module 12 is not limited to the above-described example, and the fixing members may be formed integrally by insertion molding at one time. In this case, in the inside of a die for molding, the plurality of pipes 1 are arrayed in parallel with one another in a two-dimensional form.

Next, as shown in FIGS. 1A to 1C, walls 51 or 52 projecting toward the outside of the heat exchange module 12 are provided on outer portions of the respective fixing members. Each of the walls 51 and 52 has a through hole that goes through the wall in the thickness direction. In the present embodiment, the outer portions of the fixing members are outer portions (outer faces) of the pipe array holding members 9a to 9d, and portions (faces) exposed on surfaces of the heat exchange module. Further, in the present embodiment, the walls 51 and 52 are provided on the uppermost faces of the pipe array holding members 9a to 9d of the pipe groups 10 positioned in the uppermost layer, and on the lowermost faces of the pipe array holding members 9a to 9d of the pipe group 10 positioned in the lowermost layer.

More specifically, the wall 51 or 52 is mounted by mounting flow path forming members 50, each of which has the walls 51 and 52, onto the heat exchange module 12. Further specifically, a total of four of the flow path forming members 50 are mounted, two of which are mounted on the pipe group 10 positioned in the uppermost layer and the other two of which are mounted on the pipe group 10 positioned in the lowermost layer. It should be noted that the present embodiment is not limited to this example, and the embodiment may be such that the flow path forming members 50 are mounted only on the pipe group 10 positioned in either the uppermost layer or the lowermost layer.

Here; a specific configuration of the flow path forming member 50 is described, with reference to FIGS. 2A to 2D. As shown in FIGS. 2A to 2D, the flow path forming member 50 has the walls 51 and 52. The walls 51 and 52 are connected in an opposed state at a certain distance from each other via a plurality of connecting members 55. The distance between the walls 51 and 52 is set according to a distance between an outer-side pipe array holding member and an inner-side pipe array holding member adjacent thereto, that is, the distance between the pipe array holding member 9a and the pipe array holding member 9b, and the distance between the pipe array holding member 9c and the pipe array holding member 9d.

Further, in the flow path forming member 50, the wall 51 is provided with a through hole 53 that goes through the wall in the thickness direction (see FIG. 2D). The wall 52 also is provided with a through hole 54 that goes through the wall in the thickness direction (see FIG. 2D). The through holes 53 and 54 are provided so that central axes thereof coincide with each other.

Further, to facilitate the mounting of the flow path forming members 50 to the pipe array holding members 9a to 9d, a plurality of protrusions 61 and a plurality of recesses 60 are formed below the walls 51 and 52, respectively (see FIGS. 2A, 2C, and 2D). More specifically, a plurality of protrusions 61 are formed so as to be engaged with a plurality of recesses 11 of the pipe array holding members 9a to 9c exposed on surfaces of the heat exchange module. The plurality of recesses 60 are formed so as to be engaged with the plurality of pipes 1 composing the pipe group 10 positioned in the uppermost layer or the lowermost layer. Still further, the plurality of protrusions 61 and the plurality of recesses 60 are arrayed in a row along the walls 51 and 52. One row of the plurality of protrusions 61 and one row of the plurality of recesses 60 are formed for each wall.

Therefore, when the flow path forming members 50 shown in FIGS. 2A to 2D are mounted on the heat exchange module 12, the pipe group 10 positioned in the uppermost layer and the pipe group 10 positioned in the lowermost layer, the wall 51 or the wall 52 protrudes in the stacking direction from each of the pipe array holding members. For example, as shown in FIG. 1C, in the pipe group 10 positioned in the uppermost layer, the wall 52 protrudes from the outer-side pipe array holding member 9a, while, from the inner-side pipe array holding member 9b adjacent thereto, the wall 51 protrudes. Still further, from the outer-side pipe array holding member 9d positioned on the opposite side, the wall 51 of another flow path forming member 50 protrudes, while, from the inner-side pipe array holding member 9c adjacent thereto, the wall 52 protrudes. Still further, in the present embodiment, the mounting of the flow path forming members 50 is carried out by the adhesion or fusion of each pipe array holding member and each flow path forming member 50, and they are brought into close contact with each other without interstices.

Further, as shown in FIGS. 2A to 2D, the walls 51 and 52 are formed so that a flow path member 63 (FIGS. 3A and 3B) that makes the through hole 53 and the through hole 54 communicate with each other can be placed between the walls 51 and 52. More specifically, on the wall 52 side (the flow path member side) of the wall 51, a pressing part 56 is provided that protrudes toward the wall 52. On the wall 51 side (the flow path member side) of the wall 52, a pressing part 57 is provided that protrudes toward the wall 51. Still further, the pressing part 56 is formed so that the through hole 53 pierces the center of the pressing part 56, while the pressing part 57 is formed so that the through hole 54 pierces the center of the pressing part 57.

As shown in FIGS. 2B and 2C, on the periphery of the opening of the through hole 53 on the wall 52 side of the wall 51, that is, on the outer portion of the pressing part 56, protrusions 58 for positioning the flow path member 63 (see FIG. 3 described below) are formed. Likewise, on the periphery of the opening of the through hole 54 on the wall 51 side of the wall 52, that is, on the outer portion of the pressing part 57, protrusions 59 for positioning the flow path member 63 are provided.

It should be noted that in the present embodiment, the flow path forming member 50 is formed by integral molding. However, the present embodiment is not limited to this example, and the flow path forming member 50 may be configured so that respective parts thereof are formed with separate components.

Subsequently, the flow path member 63 is mounted between the adjacent walls 51 and 52 of the flow path forming member 50 (see FIG. 5 described later). A total of four of the flow path members 63 are mounted, one for each flow path forming member 50. More specifically, as shown in FIGS. 3A and 3B, the flow path member 63 is composed of an annular member (O-ring) formed by an elastic material such as a rubber material or a resin material. The distance between the pressing part 56 and the pressing part 57 is set so as to be smaller than the thickness of the annular member (O-ring) composing the flow path member 63.

For this reason, when the flow path member 63 is placed between the walls 51 and 52, that is, between the pressing parts 56 and 57, the flow path member 63 is pressed by the pressing parts 56 and 57, thereby being subjected to elastic deformation, into a state of being fitted between the walls 51 and 52 (see FIG. 5 described later). Consequently, the through hole 53, an inner circumferential part 64 of the flow path member 63, and the through hole 54 forms one flow path (see FIG. 6 described later). Still further, since the flow path member 63 is brought into close contact with the pressing parts 56 and 57 without gaps, fluid flowing through this flow path is prevented from leaking.

Next, as shown in FIG. 5, the heat exchange module 12 (see FIGS. 1A to 1C) on which the flow path forming member 50 is mounted is housed in the housing 2 (see FIG. 4). More specifically, in the present embodiment, as shown in FIG. 4, the housing 2 is composed of a housing top part 2*a* and a housing bottom part 2*b*. Each of the housing top part 2*a* and the housing bottom part 2*b* has a channel-shape cross section (an angular-U-shape cross section). When they are bonded in a state in which the insides of the channels of these are opposed to each other, an opening 15*a* is formed at one end of the housing 2, while an opening 15*b* is formed at the other end thereof (see FIG. 6). The openings 15*a* and 15*b* are opposed to each other, and through the openings 15*a* and 15*b*, the ends of the pipes 1 are exposed to the outside of the housing 2.

Further, since blood is guided into the housing 2 in a direction crossing the direction in which the openings 15*a* and 15*b* are opposed (hereinafter referred to as an opposing direction of the openings 15*a* and 15*b*), an inlet 4 for blood is formed on a principal face of the housing top part 2*a*. In the example shown in FIG. 4, the inlet 4 has a shape like a tower protruding from the principal face of the housing top part 2*a*. On a principal face of the housing bottom part 2*b*, at a position opposite to the inlet 4, a circular opening is formed. This opening constitutes an outlet 5 for discharging blood. An axis that passes through the centers of the inlet 4 and the outlet 5 perpendicularly crosses an axis that passes through the centers of a pair of openings 15*a* and 15*b*.

Therefore, in the present embodiment, as shown in FIG. 5, first, the heat exchange module 12 is placed in the housing bottom part 2*b* in a manner such that the central axes of the pipes 1 coincide with the opposition direction of the openings 15*a* and 15*b*, and further, the outlet 5 faces the pipe group 10 positioned in the lowermost layer. Next, the housing top part 2*a* is bonded with the housing bottom part 2*b* in a manner such that the inlet 4 faces the pipe group 10 positioned in the uppermost layer.

Further, here, in the present embodiment, outer portions of the pipe array holding members 9*a* to 9*d* of the pipe groups 10, which are exposed on surfaces of the heat exchange module 12 and on which the flow path forming members 50 are not mounted, are fixed to and brought into contact with the inner surfaces of the housing 2 with use of an adhesive. Ceiling faces (top faces) of the walls 51 and 52 are fixed to and brought into contact with inner surfaces of the housing 2 with use of an adhesive.

Further, as shown in FIG. 4, on principal faces of the housing upper part 2*a* and the housing lower part 2*b*, openings 6 are formed so that the flow path forming members 50 are exposed therethrough. Still further, along boundaries between the principal faces and the side faces of the housing upper part 2*a* and the housing lower part 2*b*, openings 13 are formed. Still further, on side faces of the housing upper part 2*a* and the housing lower part 2*b*, notches 14 are formed so as to form openings on the side faces of the housing 2 when the housing upper part 2*a* and the housing lower part 2*b* are bonded.

Further, the openings 6, the openings 13, and the notches 14 are formed so as to face portions between the outer-side pipe array holding members and the inner-side pipe array holding members adjacent thereto. Therefore, as shown in FIG. 7 described later, the openings 6, the openings 13, and the notches 14 function as outlets for discharging liquid retained in the gaps 7 formed between first and second sealing members 3*a*, 3*b*, and the third sealing member 3*c* at the center. Still further, particularly, the openings 6 also function as openings through which the flow path members 63 are taken out after the step for forming the sealing members is carried out as shown in FIG. 6 described later.

Next, as shown in FIG. 6, while the housing 2 is rotated around an axis that passes through the center of the inlet 4 and the center of the outlet 5 of the housing 2, a resin material is filled in the inside of the housing 2, whereby the first, second, and third sealing members 3*a*, 3*b*, and 3*c* are formed (see FIG. 7). Further, with the third sealing member 3*c*, a flow path 8 (see FIG. 7) for guiding blood introduced through the inlet 4 to the outlet 5 is formed. It should be noted that in FIG. 6, the heat exchange module 12 is shown by a side view.

More specifically, in the present embodiment, the housing 2 is fixed on a rotation table 16 in a state in which the opening 15*a* on one side is closed by a shielding member 18*a*, the opening 15*a* on the other side is closed by a shielding member 18*b*, and further, the outlet 5 is closed by a shielding member 17. Here, a rotation axis of the rotation table 16 and an axis that passes through the center of the inlet 4 and the center of the outlet 5 of the housing 2 coincide with each other.

Further, an injection pot 19 for retaining a resin material 24 to be filled is placed on a central portion of the top face of the housing 2. The injection pot 19 is provided, with supply pipes 20 on its outer portion. This is intended to send out the resin material 24 efficiently by utilizing centrifugal force. In the example shown in FIG. 6, a Y-shaped pipe whose one opening is closed is used as each of the supply pipe 20. The supply pipes 20 are placed at two positions opposite to each other. The injection pot 19 is configured to close the inlet 4 when it is placed on the housing, in order to prevent the resin material 24 from intruding through the inlet 4.

Further, through holes 23 are provided in the shielding members 18a and 18b, so as to communicate with the openings 15a and 15b of the housing 2, respectively. Moreover, an injection pipe 22 is attached to each through hole 23 so that the injection pipe 22 and the through hole 23 communicate with each other. In the example shown in FIG. 6, as the injection pipe 22 also, a Y-shaped pipe whose one opening is closed is used. Each injection pipe 22 is connected with each supply pipe 20 of the injection pot 19 via a pipe 21.

Therefore, when the resin material 24 is retained in the injection pot 19 and the rotation table 16 is rotated in the foregoing state, the resin material 24 is transferred to the supply pipes 20, the pipes 21, and the injection pipes 22 by the centrifugal force caused by the rotation. The resin material 24 is filled in interstices (hereinafter referred to as "first housing space") around the pipes 1 present between the opening 15a of the housing 2 on the left side and the outer-side pipe array holding member (9a or 9d) on the left side, and in interstices (hereinafter referred to as "second housing space") around the pipes 1 present between the opening 15b of the housing 2 on the right side and the outer-side pipe array holding member (9d or 9a) on the right side.

Further, the resin material 24 supplied to the first and second housing spaces is pushed by the resin material 24 transferred later, and a part of the resin material 24 flows through flow paths formed by the through holes 53 and 54 of the flow path forming members 50 and the flow path members 63. Besides, the resin material 24 having passed through the flow paths enter the interstices around the pipes 1 present between the inner-side pipe array holding members 9b and 9c (hereinafter referred to as "third housing space"), whereby the third housing space is filled with the resin material 24.

Still further, when the filling of the resin material in the first to third housing spaces is completed and the resin material is cured, the flow path members 63 are removed. With this, the paths that connect the first and second housing spaces with the third housing space are closed, whereby these housing spaces are separated. As a result, it is possible to prevent cold/hot water from going along the through holes 53, 54 and the flow path members 63 and intruding into the third housing space, and to prevent blood from going along the same and intruding into the first or second housing space.

Consequently, as shown in FIG. 7, a heat exchanger according to the present embodiment is obtained. Like the conventional heat exchanger shown in FIGS. 9 and 10 described in the "Background Art" section, the heat exchanger according to the present embodiment also includes a first sealing member 3a, a second, sealing member 3b, and a third sealing member 3c. It should be noted that the illustration of the housing 2 is omitted in FIG. 7.

The first sealing member 3a is formed with the resin material 24 filled in the first housing space. The second sealing member 3b is formed with the resin material 24 filled in the second housing space. The third sealing member 3c is formed with the resin material 24 filled in the third housing space.

Further, since the resin material 24 filled in the third housing space is subjected to the centrifugal force caused by the rotation, a cylindrical space in which the resin material 24 is not filled is formed in the third housing space. The cylindrical space forms a flow path (blood flow path) 8 through which blood introduced through the inlet 4 is guided to the outlet 5.

Blood passing through the flow path 8 is subjected to heat exchange, via the pipes 1, with cold/hot water passing through the pipes 1. Besides, the gaps 7 are formed between the first sealing member 3a and the third sealing member 3c, and between the second sealing member 3b and the third sealing member 3c, by the pipe array holding members 9a to 9d.

In this way, the heat exchanger manufactured by the method for manufacturing the heat exchanger according to the present embodiment has a configuration identical to that of the conventional heat exchanger. However, in the present embodiment, as shown in FIG. 6, the resin material 24 for forming the third sealing member 3c (see FIG. 7) is transferred to the third housing space through the flow path formed with the through holes 53 and 54 of the flow path forming members 50 and the flow path members 63. Thus, a space where conventionally air reservoir tends to occur is used as a flow path for the resin material 24.

Therefore, in the present embodiment, as compared with the conventional heat exchanger, the occurrence of air reservoir in the first sealing member 3a and the second sealing member 3b is suppressed, and the degradation of air tightness and reliability of these also is suppressed. In the other words, according to the method for manufacturing the heat exchanger according to the present embodiment, the occurrence of air reservoir is suppressed, whereby the degradation of air tightness and durability of the sealing members of the heat exchanger obtained can be suppressed also.

Figure 13:
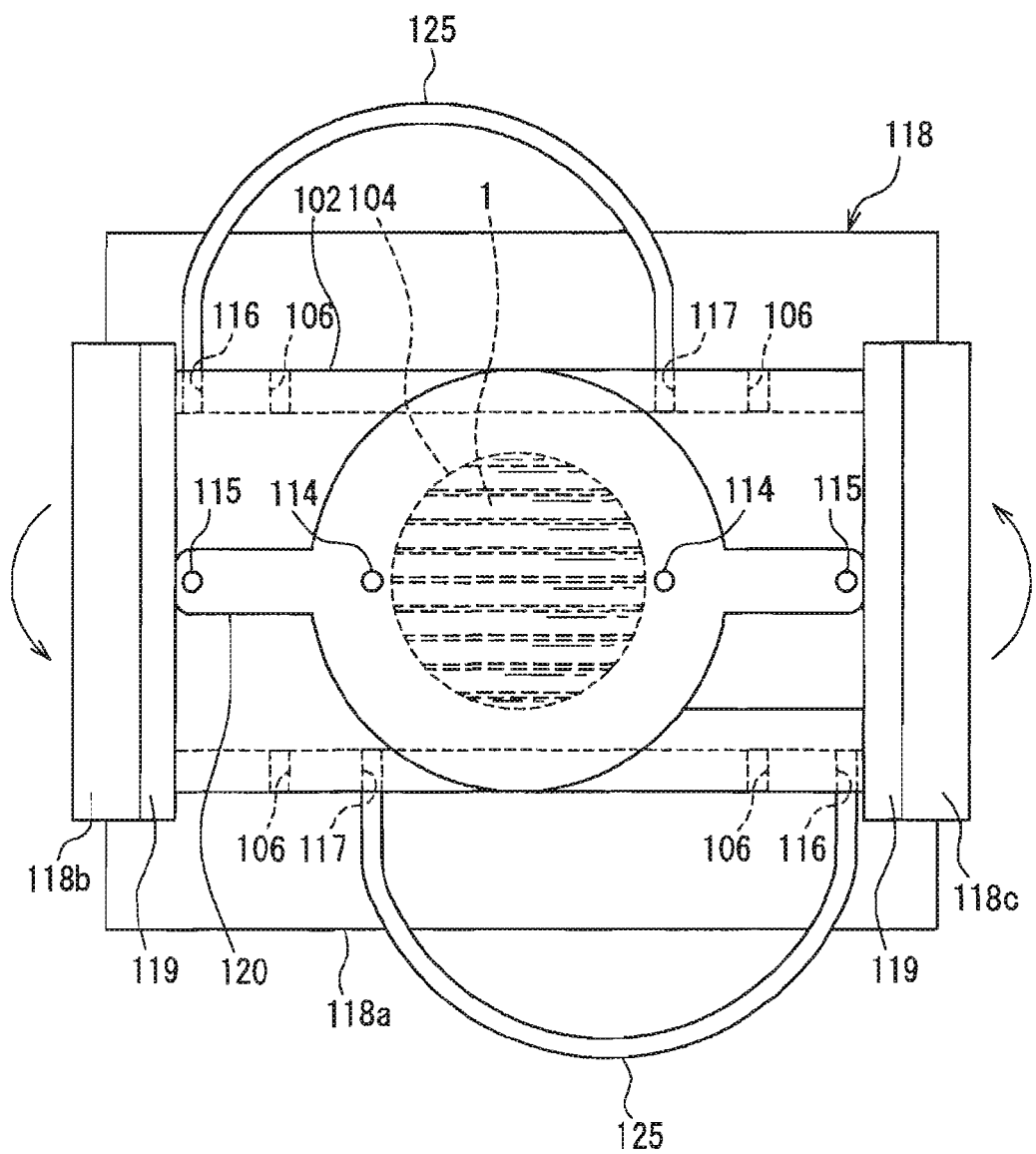
FIG. 13 is a top view illustrating the state in which the housing is attached to a jig so that sealing members are formed.
Figure 14:
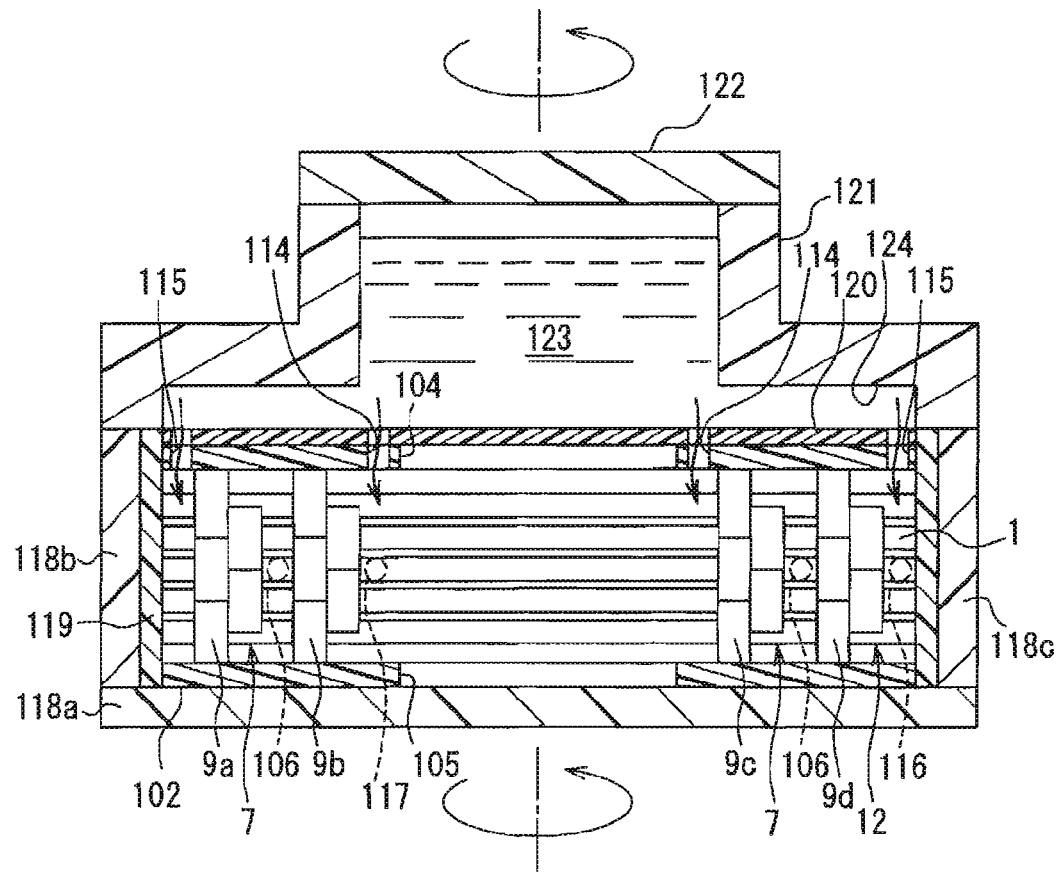
FIG. 14 is a cross-sectional view showing a step for forming the sealing members.

Further, in the method for manufacturing the heat exchanger according to the present embodiment, different from the conventional method for manufacturing the heat exchanger shown in FIG. 13, which is described in the "Background Art" section, it is unnecessary to connect the first housing space with the third housing space, and to connect the second housing space with the third housing space, via pipes. For this reason, with the method for manufacturing the heat exchanger according to the present embodiment, the possibility of suspending the process is reduced, as compared with the conventional method for manufacturing the heat exchanger, whereby the percent of defective products can be reduced.

In the present embodiment, the positions of the through holes 53 and 54 formed in the flow path forming members 50 are not limited particularly. However, as shown in FIGS. 1A to 1C, FIGS. 2A to 2D, and FIG. 5, the through holes 53 and 54 preferably are positioned on a line that is parallel with the axis passing through the respective centers of the openings 15a and 15b and that perpendicularly crosses the rotation axis of the housing 2. In other words, the through holes 53 and 54 preferably are provided at the centers of the walls 51 and 52. The reason for this is as follows: in the present embodiment, since the axis passing through the centers of the inlet 4 and the outlet 5, which is the rotation axis, and the axis passing through the respective centers of the openings 15a and 15b cross perpendicularly, air reservoir tends to occur most likely in a region on the above-described line owing to the centrifugal force.

Further, in the present embodiment, as shown in FIG. 6, the resin material 24 is injected through the openings 15a and 15b of the housing 2, but the configuration is not limited to this. For example, the configuration may be such that through holes that communicate with the first housing space and the second housing space are provided on principal faces or side faces of the housing 2 so that the resin material 24 is injected through these through holes. Still further, the configuration may be such that a through hole that communicates with the third housing space is provided on a principal face or a side face of the housing 2 so that the resin material 24 is filled in the third housing space through both the foregoing through hole and the flow paths of the flow path forming members 50.

Still further, as shown in FIGS. 1 to 7, in the present embodiment, the flow path forming members 50 and the flow path members 63 are separate components, but the present embodiment is not limited to this example. In other words, in the present embodiment, the flow path forming member may have a configuration in which the walls 51 and 52 are connected with each other by a tubular member that communicates with the through holes of the respective walls.

In the present embodiment, examples of the resin material for forming the sealing members 3a to 3c may be thermosetting resins such as silicon resins, polyurethane resins, and epoxy resins. Among these, polyurethane resins and epoxy resins are preferable, in view of their excellent adhesion to a material forming the pipes 1 (e.g., a metal material) and a material forming the housing 2 (e.g., a resin material such as a polycarbonate resin).

Figure 8:
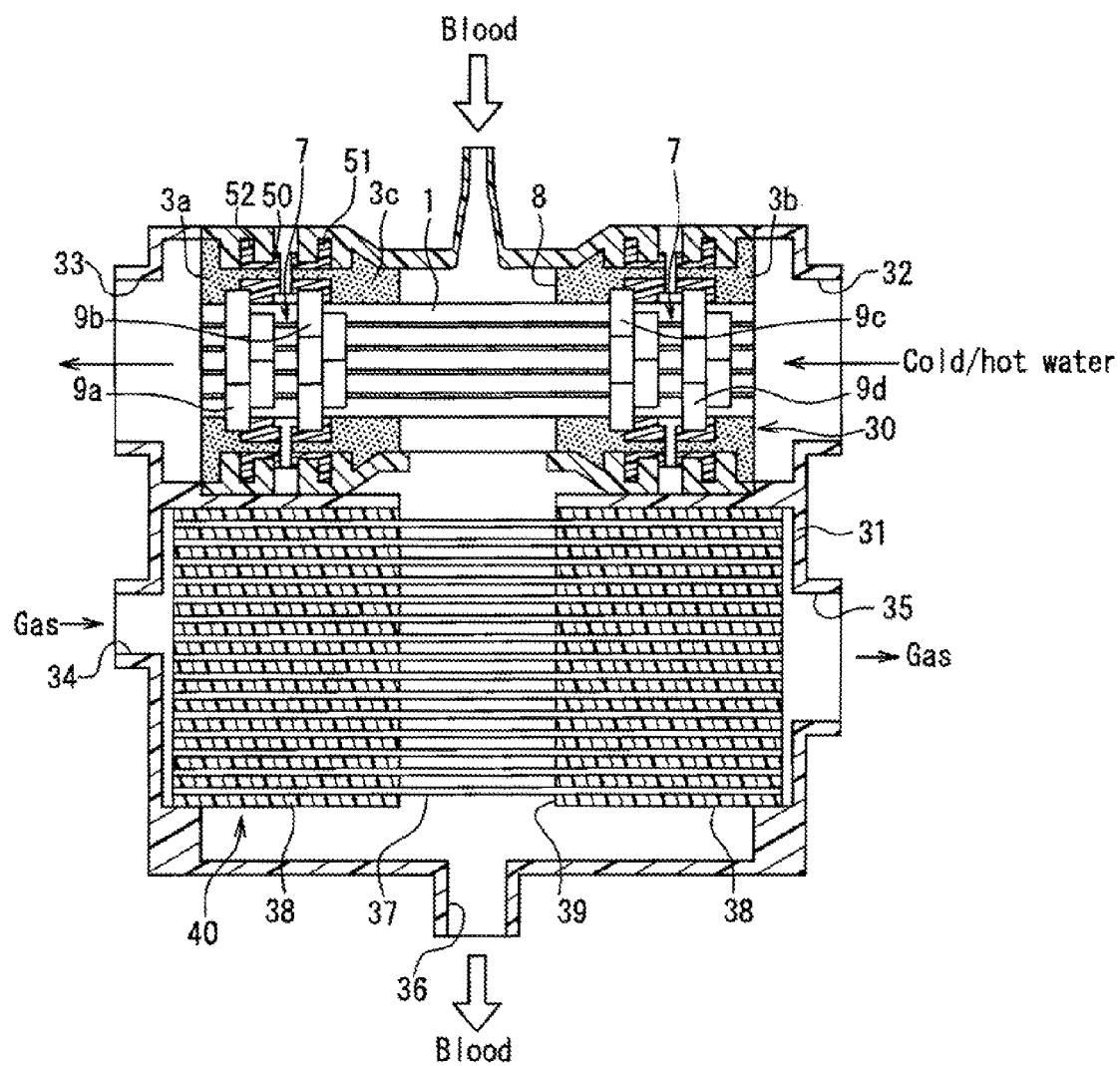
FIG. 8 is a cross-sectional view showing a heart-lung machine manufactured by using the method for manufacturing the heat exchanger according to the present embodiment.
Figure 9A:
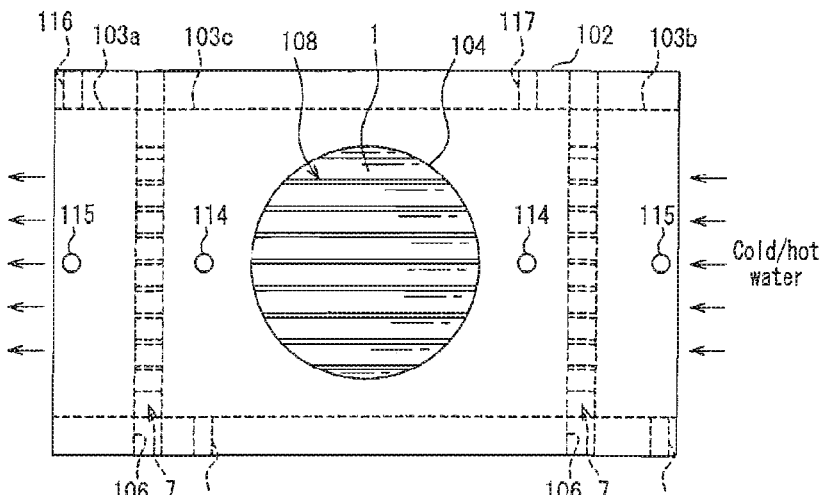
FIGS. 9A to 9C show a configuration of a conventional heat exchanger.
Figure 9B:
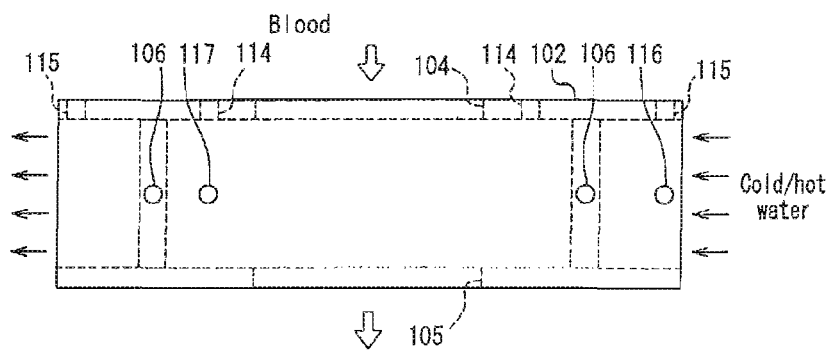
Figure 9C:
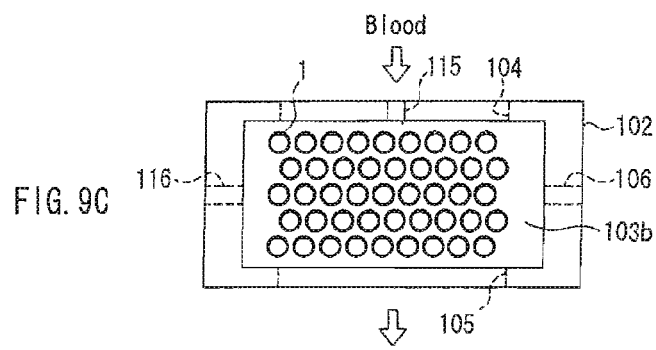
Figure 10:
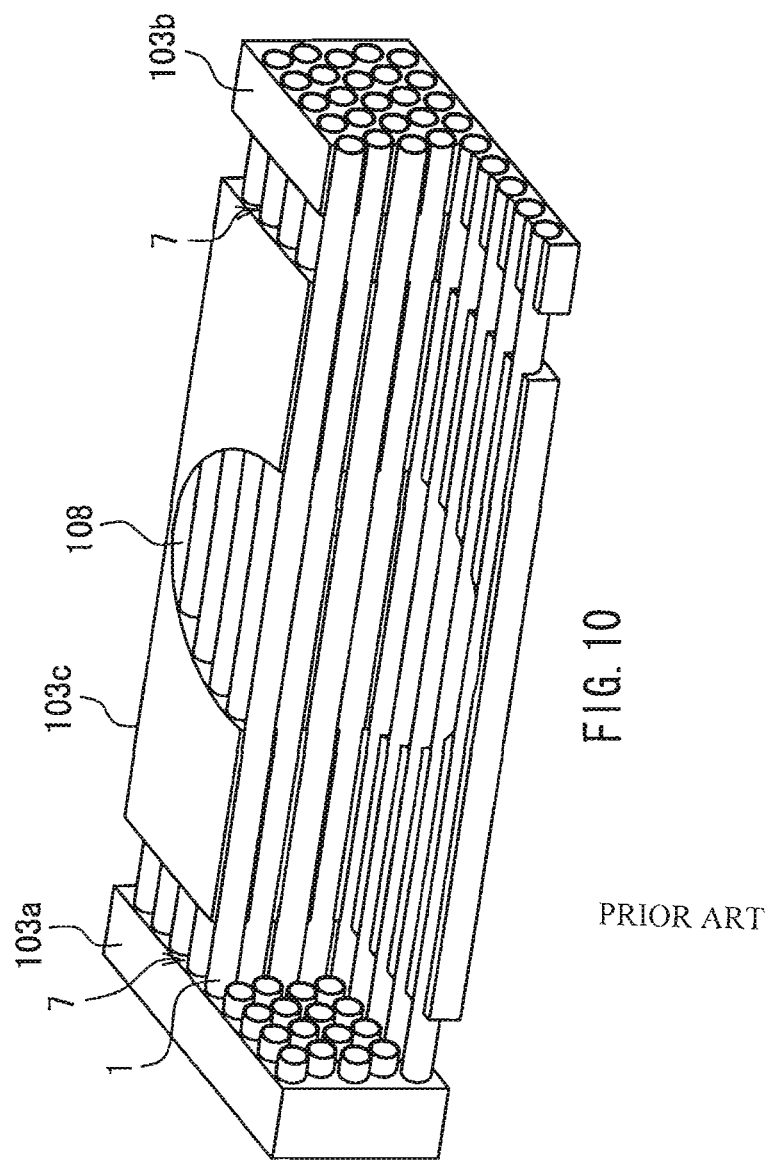
FIG. 10 is a partially cut-off perspective view illustrating the inside of a housing of the heat exchanger shown in FIGS. 9A to 9C.
Figure 11A:
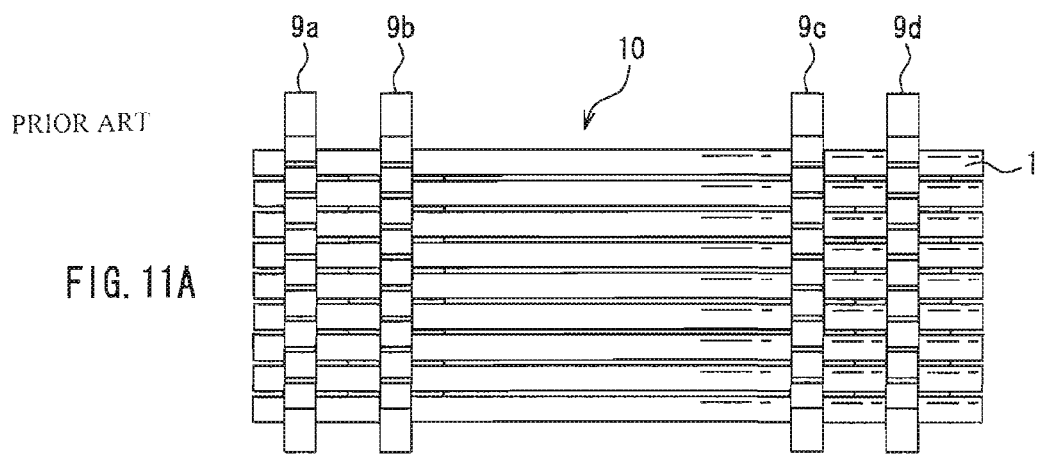
FIGS. 11A to 11C show pipe groups composing a heat exchange module.
Figure 11B:
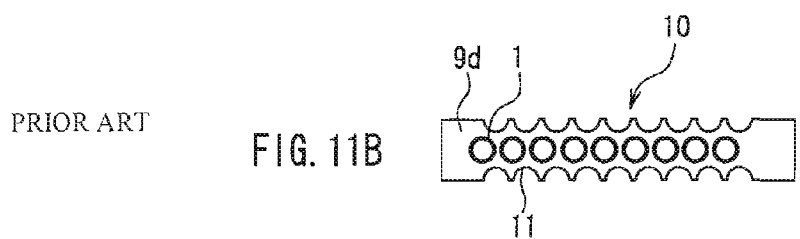
Figure 11C:
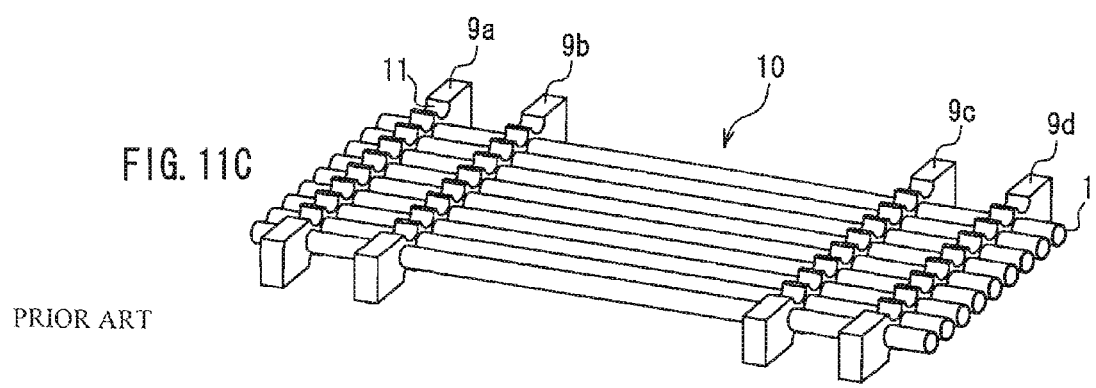

Further, the method for manufacturing the heat exchanger according to the present embodiment can be used for manufacturing a heart-lung machine equipped with the heat exchanger. FIG. 8 is a cross-sectional view showing a heart-lung machine manufactured by using the method for manufacturing the heat exchanger according to the present embodiment. It should be noted that in FIG. 8, portions denoted with the same reference numerals shown in FIGS. 1 to 7 are the same as the portions denoted with the foregoing reference numerals in FIGS. 1 to 7.

As shown in FIG. 8, the heart-lung machine is equipped with a heat exchanger 30 and an artificial lung 40, which are housed in a housing 31. The housing 31 is provided with a cold/hot water introducing path 32 for introducing cold/hot water for heat exchange, a cold/hot water discharging path 33 for discharging cold/hot water, a gas introducing path 34 for introducing oxygen gas, and a gas discharging path 35 for discharging carbon dioxide, etc., in blood.

The heat exchanger 30 is identical to the heat exchanger shown in FIG. 7. In FIG. 7, the heat exchange module 12 is shown in a side view. In the heat exchanger 30 shown in FIG. 7, cold/hot water flows through the pipes 1, while blood of a patient flows through the flow path 8. The artificial lung 40 includes a plurality of hollow fiber membranes 37 and sealing members 38. The sealing members 38 seal the hollow fiber membranes 37 so as to prevent blood from intruding into the gas introducing path 34 and the gas discharging path 35. The sealing by the sealing members 38 is performed in a manner such that both ends of hollow fibers forming the hollow fiber membranes 37 are exposed. The gas introducing path 34 and the gas discharging path 35 communicate with each other via the hollow fibers forming the hollow fiber membranes 37.

Further, a space in the artificial lung 40 where the sealing members 38 are not present forms a blood flow path 39, and the hollow fiber membranes 37 are exposed in the blood flow path 39. Still further, a blood inlet side of the blood flow path 39 communicates with an outlet side of the flow path 8 of the heat exchanger 30.

Therefore, blood subjected to heat exchange through the flow path 8 flows into the blood flow path 39, where the blood comes into contact with the hollow fiber membranes 37. Here, oxygen gas flowing through the hollow fiber membranes 37 is captured by the blood. The blood thus having captured oxygen gas is discharged via a blood outlet 36 provided in the housing 31 to the outside, thereby being returned to the patient. On the other hand, carbon dioxide in the blood is captured by the hollow fiber membranes 37, and is discharged through the gas discharge path 35 thereafter.

Thus, in the heart-lung machine shown in FIG. 8, the blood temperature is controlled by the heat exchanger 30, and blood having been subjected to the temperature control is subjected to gas exchange by the artificial lung 40. Here, even if the sealing of the heat exchanger 30 has a seal leakage so as to cause so as to cause cold/hot water flowing through the pipes 1 to flow out, the cold/hot water is retained in the gaps 7, and thereafter is discharged to the outside. Therefore, with the artificial heart-lung machine shown in FIG. 8, the leakage through the sealing can be detected, whereby the contamination of blood with cold/hot water can be suppressed.

INDUSTRIAL APPLICABILITY

As described above, the present invention makes it, possible to obtain a heat exchanger having excellent air tightness and reliability of sealing. The heat exchanger, the method for manufacturing the heat exchanger, and the method for manufacturing the heart-lung machine according to the present invention have industrial applicability.

The invention claimed is:

1. A method for manufacturing a heat exchanger, the heat exchanger including pipes through which a first fluid flows, and a housing, wherein
   the housing has a pair of openings that expose ends of the pipes on both sides, an inlet for introducing a second fluid into the housing, and an outlet provided so as to be opposed to the inlet, the outlet being for discharging the second fluid, and
   the second fluid comes into contact with surfaces of the pipes,
   the method comprising the steps of:
   (a) forming a heat exchange module that includes a plurality of pipes arrayed in parallel with one another in a two-dimensional form, and fixing members that are present in interstices around the pipes to hold the array of the plurality of pipes, wherein four pieces of the fixing members are arranged along a central axis direction of the pipes with spaces therebetween;
   (b) providing walls on respective outer peripheral portions of the fixing members, wherein each of the walls has a through hole going through in a thickness direction of the wall, and protrudes toward outside of the heat exchange module;
   (c) arranging flow path members, each of which is arranged between the walls on the outer-side fixing member positioned closely to an end of the tube and on the inner-side fixing member adjacent to the outer-side fixing member so as to communicate with the through holes provided in the walls;
   (d) housing the heat exchange module into the housing, and bringing parts of the outer peripheral portions of the fixing members where the walls are not provided, and the walls, into close contact with inner surfaces of the housing; and
   (e) while rotating the housing around an axis that passes through the centers of the inlet and the outlet, filling a resin material into interstices around the pipes present between one of the openings of the housing and the outer-side fixing member adjacent thereto, interstices around the pipes present between the other opening of the housing and the outer-side fixing member adjacent thereto, and interstices around the pipes present between the two inner-side fixing members, and further, forming a flow path between the two inner-side fixing members through which the second fluid introduced through the inlet is guided to the outlet.

2. The method for manufacturing a heat exchanger according to claim 1, wherein
in the step (a), the heat exchange module is formed by the steps of:
forming a pipe group that includes two or more of the pipes arrayed in a row in parallel with one another, and pipe array holding members, each of which is present in gaps between the pipes to hold the array of the two or more pipes, four pieces of the pipe array holding members being arranged along the central axis direction of the pipes with spaces therebetween; and
stacking a plurality of the pipe groups, wherein the pipe array holding members of each pipe group are brought into close contact with the pipe array holding members of another pipe groups immediately above and below the said group in the central axis direction, so that the fixing members are formed with the pipe array holding members of the pipe groups, and
in the step (b), on at least one of the pipe group positioned in an uppermost layer and the pipe group positioned in a lowermost layer, the walls are provided on the outer-side pipe array holding member positioned closely to the ends of the tubes and the inner-side pipe array holding member adjacent to the outer-side tube array holding member in a manner such that the walls are opposed to each other.

3. The method for manufacturing a heat exchanger according to claim 2, wherein
in the step (b), on both of the pipe group positioned in the uppermost layer and the pipe group positioned in the lowermost layer, the walls are provided on the two outer-side pipe array holding members and the two inner-side pipe array holding members.

4. The method for manufacturing a heat exchanger according to claim 1, wherein
the axis that passes through the centers of the inlet and the outlet perpendicularly crosses an axis that passes through the centers of the pair of openings, and the through holes are provided so as to be positioned on a line that is parallel with the axis that passes through the centers of the pair of openings, and that perpendicularly crosses a rotation axis of the housing.

5. The method for manufacturing a heat exchanger according to claim 1, further comprising the step of:
after the step (e), removing the flow path members.

6. The method for manufacturing a heat exchanger according to claim 1, wherein
the flow path members are formed with annular members having elasticity, and
in the step (c), the annular members are fitted between the walls in a state of being deformed elastically.

7. The method for manufacturing a heat exchanger according to claim 1, wherein
in the step (b), flow path forming members, each of which has two of the walls and is formed by connecting the walls in a state in which one wall and the other wall are opposed to each other, are arranged in a manner such that the one wall protrudes from the outer-side fixing member, while the other wall protrudes from the inner-side fixing member adjacent to the said outer-side fixing member.

8. The method for manufacturing a heat exchanger according to claim 1, wherein in the step (e),
the resin material is supplied to the interstices around the pipes present between one of the openings of the housing and the outer-side fixing member adjacent thereto, and the interstices around the pipes present between the other opening of the housing and the outer-side fixing member adjacent thereto, and
the resin material is supplied further to the interstices around the pipes present between the two inner-side fixing members via the through holes of the walls provided on the outer-side fixing members, the flow path members, and the through holes of the walls provided on the inner-side fixing members adjacent to the outer-side fixing members.

* * * * *